(12) United States Patent
Ertl et al.

(10) Patent No.: US 6,417,414 B1
(45) Date of Patent: Jul. 9, 2002

(54) PROCESS FOR THE PREPARATION OF 1,2-DICHLOROETHANE BY OXYCHLORINATION

(75) Inventors: Horst Ertl, Neuoetting; Peter Schwarzmaier, Kastl; Ingolf Mielke; Peter Kammerhofer, both of Burgkirchen, all of (DE)

(73) Assignee: Vinnolit Monomer GmbH & Co. KG, Ismaning (DE)

( * ) Notice: Subject to any disclaimer, the term of this patent is extended or adjusted under 35 U.S.C. 154(b) by 0 days.

(21) Appl. No.: 09/555,060

(22) PCT Filed: Nov. 19, 1998

(86) PCT No.: PCT/EP98/07444

§ 371 (c)(1),
(2), (4) Date: Jul. 31, 2000

(87) PCT Pub. No.: WO99/28280

PCT Pub. Date: Jun. 10, 1999

(30) Foreign Application Priority Data

Dec. 1, 1997 (DE) .......................... 197 53 165

(51) Int. Cl.⁷ .............................................. C07C 17/15
(52) U.S. Cl. ...................................................... 570/243
(58) Field of Search .......................................... 570/243

(56) References Cited

U.S. PATENT DOCUMENTS

| 3,256,352 A | | 6/1966 | Bohl et al. |
| 4,057,592 A | * | 11/1977 | Antonini et al. ............. 570/243 |
| 4,243,650 A | * | 1/1981 | Tsao ........................... 570/243 |

FOREIGN PATENT DOCUMENTS

| DE | 1468 488 | 12/1968 |
| DE | 41 32 030 | 4/1993 |
| DE | 195 46 068 | 6/1997 |
| DE | 196 31 382 | 2/1998 |
| DE | 197 03 857 | 8/1998 |
| EP | 0 103 940 | 3/1984 |
| GB | 1 256 245 | 12/1971 |
| GB | 1351700 | 5/1974 |
| WO | 96/26003 | 8/1996 |

* cited by examiner

*Primary Examiner*—Alan Siegel
(74) *Attorney, Agent, or Firm*—Frommer Lawrence & Haug, LLP; Ronald R. Santucci

(57) ABSTRACT

The present invention is directed to a process for preparing 1,2-dichloroethane by reacting ethene with hydrogen chloride and oxygen over a copper-containing fluidized-bed catalyst. The discharge of the catalyst from the reactor per se is avoided if the catalyst is virtually completely retained in the upper part of the reactor by means of superfine filtration.

4 Claims, No Drawings

PROCESS FOR THE PREPARATION OF 1,2-DICHLOROETHANE BY OXYCHLORINATION

This application is a 371 of PCT/EP98/07444 filed Nov. 19, 1998.

DESCRIPTION

"Oxychlorination" is understood as meaning the reaction of an alkene—in this case ethene—with hydrogen chloride and oxygen or an oxygen-containing gas, such as air, the formation of a saturated chlorinated alkane—in this case 1,2-dichloroethane, referred to below as "EDC". The reaction takes place according to the equation $$C_2H_4 + 2HCl + \tfrac{1}{2}O_2 \iff Cl-CH_2-CH_2-Cl + H_2O.$$

The byproduct of the reaction, water, can thus form corrosive hydrochloric acid with the unconverted starting material hydrogen chloride, so that correspondingly resistant—and hence expensive—materials must be used for the apparatuses.

In an embodiment of this process which is frequently carried out on an industrial scale, a fluidized bed serves as the catalyst, the catalyst essentially comprising copper chloride on an alumina carrier.

In the usual industrial processes, the fluidized catalyst is deposited in the upper part of the oxychlorination reactor by a plurality of cyclones connected in series and thus retained for the most part in the reactor. However, a small proportion passes over with the exit gas of the reaction and thus enters the EDC working-up, where it has to be separated off.

DE-A-41 32 030 discloses a process for removing abraded catalyst material which is obtained in the reaction zone in the preparation of EDC by the oxychlorination process and is removed from the reaction zone with the crude EDC gas stream, wherein the abraded catalyst material removed is separated from the crude EDC gas stream in a purification zone operated under dry conditions. In preferred embodiments of this process, the abraded catalyst material is separated off on a dust separator or in an electric filter as a purification zone, the dust separator is equipped with bag filters which are cleaned with compressed circulating gas, the abraded catalyst material deposited in the purification zone is freed from adsorbed reaction products in a downstream desorption zone, the desorption zone is operated at a temperature from 50 to 350° C., in particular from 150 to 180° C., by gassing or at reduced pressure, air, nitrogen or circulating gas is used for the gassing, and the abraded catalyst material is treated for from 0.5 to 5 hours, preferably from 1 to 2 hours, at an elevated temperature in the desorption zone. This process avoids the formation of a wastewater contaminated with heavy metal and inorganic sludge during the removal of water formed and of the washwater used in the working-up. However, the fine catalyst fraction separated off must be discarded and disposed of properly.

DE-A-195 46 068 relates to a process for reducing the catalyst consumption and contaminated catalyst wastes in the preparation of EDC by the oxychlorination process over a copper-containing fluidized-bed catalyst in a reaction zone, in which the abraded catalyst material is separated off from the crude EDC gas stream in a separation zone operated under dry conditions, wherein the abraded catalyst material is classified and specific particle fractions are recycled to the reaction zone. In preferred embodiments of this process, the abraded catalyst material is classified into a coarse fraction and a fine fraction, the coarse fraction corresponds to a particle size >5 $\mu$m and the fine fraction to a particle size <5 $\mu$m, the coarse fraction is recycled to the reaction zone, the fine fraction is aftertreated thermally at from 300 to 800° C., preferably from 600 to 800° C., the aftertreated exit gases are passed into an incineration furnace, the incineration furnace has a temperature above 900° C., preferably more than 1000° C., copper and/or aluminum are recovered from the fine fraction, the fine fraction is disposed of in a landfill in a controlled manner, and the dioxins and/or furans are removed from the abraded catalyst material. This process thus overcomes the disadvantages of the process according to DE-A-41 32 030, but at the cost of considerable cost of apparatuses and work for operating and maintaining them.

Common to both known processes is the fact that the separation of the discharged fine catalyst fractions is carried out in a zone separated from the reactor.

It has now been found that the discharge of the catalyst from the reactor itself can be avoided if the catalyst is virtually completely retained in the upper part of the reactor by means of superfine filtration.

The invention therefore relates to a process for the preparation of EDC by oxychlorination, ethene reacting with hydrogen chloride and oxygen or an oxygen-containing gas over a fluidized bed comprising a copper-containing catalyst, and the reaction gas emerging from the reactor being freed from catalyst in the reactor by a superfine filtration and said catalyst thus being retained in the reactor.

"Superfine filtration" is understood as meaning a process which retains the fine fraction of the oxychlorination catalyst. While the cyclones customary to date allowed a fine fraction below about 10 $\mu$m to enter the product stream, according to the invention, particles below about 1 $\mu$m are retained, i.e. virtually the entire catalyst.

Surprisingly, it was furthermore found that, according to the invention, the separation of a coarse catalyst fraction by means of the cyclones can be dispensed with. Thus, the coarse fraction and fine fraction of the catalyst are retained in one step by the superfine filtration. This has a number of advantages.

By dispensing with the cyclones, not only are the cost of apparatuses and the inconvenient maintenance of these poorly accessible components avoided but it is also possible significantly to reduce the installed height of the reactors. This makes the reactor considerably cheaper and of course also reduces the space required in the plant and hence the construction cost.

In comparison, the apparatuses—known per se—required for the superfine filtration can be easily installed in readily accessible form in the upper part of the reactor, for example in each case in separate connections which permit easy maintenance or rapid replacement of the filter apparatus with only short downtimes. Furthermore, such a design permits individual apparatuses to be put out of operation during ongoing operation.

For example, filter candle apparatuses made of material suitable for the EDC preparation are suitable, for example metals, alloys, glass or ceramic, preferably with filter candles of porous, sufficiently corrosion-resistant metal, such as sintered metal powders or woven wire fabrics or nonwoven wire fabrics of stainless steel or highly corrosion-resistant alloys, as commercially available under the names ®INCONEL (trademark of Inco Ltd.; nickel-chromium alloy), ®MONEL (trademark of Inco Ltd.; nickel-copper alloy), ®HASTELLOY (nickel alloy), and of porous ceramic material.

Furthermore, fabric filters of sufficiently heat-resistant, in particular fluorinated plastics, such as polytetrafluoroethylene, for example bag filters, can be used.

All superfine filters which retain particles of about 1 μm or above, i.e. preferably allow through only particles below about 0.8 μm, in particular below about 0.5 μm or even below 0.2 μm, are suitable.

The separation of the catalyst filter cake built up on filter materials is effected—as usual—advantageously by passing through gas countercurrently, preferably reaction gases (starting materials),. inert gases or circulated gas (recycled gas), for example in pulses, preferably at regular time intervals, or as soon as a predetermined thickness of the filter cake has built up and/or a corresponding pressure drop has occurred.

It is very surprising that, with this simple arrangement of the superfine filter in the reactor itself, discharge of the catalyst can be reliably avoided and hence the effort required to date involving the recovery and working up, which was always associated with losses, can be dispensed with. In addition, the abrasion caused by the catalyst, in the plant part up to discharge of the fine fraction can also be avoided.

By fluidizing the catalyst, the particle size spectrum is shifted toward smaller particles in the course of time. Since this process is associated with an increase in the size of the effective surface area, this is linked to an increase in catalyst activity. If this is undesired or if it is required after a relatively long operation, the undesired fine fraction can be easily separated during a brief interruption of the process. The disadvantages occurring in the known processes with the continuous discharge of the fine fraction thus do not occur here.

A process for working up 1,2-dichloroethane from the oxychlorination has already been proposed, wherein the gaseous products from the oxychlorination reactor are freed from entrained catalyst and then acidic components are washed out in a wash zone with an alkaline wash solution (German Patent Application 197 03 857.3 of Feb. 3, 1997). In preferred embodiments of the process, the alkaline wash solution is fed countercurrently, and a part-stream of the gaseous products is removed between catalyst removal and wash zone and is analyzed. An apparatus for carrying out said process was furthermore proposed, which apparatus comprises an oxychlorination reactor and a gas removal line which leads via a catalyst separator into a wash zone in which acidic components are separated off using an alkaline wash solution. Advantageously, a branch line between catalyst separator and wash zone is furthermore provided for analytical monitoring of the reaction.

A process for the preparation of 1,2-dichloroethane from ethylene, hydrogen chloride and oxygen or an oxygen-containing gas, unconverted hydrogen chloride being washed out of the reaction mixture with water, a parameter being determined in the wash water and this parameter being used for at least partial neutralization of the hydrogen chloride, was furthermore proposed, wherein the parameter is additionally used for controlling the amount of hydrogen chloride used. Advantageously, the electrical conductivity is determined here as the parameter, the wash water is circulated and/or the conductivity of the outflowing and additionally of the inflowing washwater is measured (German Patent Application 196 31 382.1 of Aug. 2, 1996). This process, too, can be advantageously combined with the process according to the invention, optionally also in combination with the process proposed in German Patent Application 197 03 857.3.

Otherwise, the oxychlorination process is carried out in a manner known per se:

The temperatures in the reaction zone of the reactor are from 200 to 270° C., preferably from 215 to 230° C. and in particular, from 220 to 225° C. The pressures are from $2.5 \cdot 10^5$ to $5 \cdot 10^5$ Pas, preferably from $3 \cdot 10^5$ to $4 \cdot 10^5$ Pas, in particular from $3.4 \cdot 10^5$ to $3.5 \cdot 10^5$ Pas (gage pressure in each case).

Up to 1.92 mol of hydrogen chloride and up to 0.53 mol of oxygen are used per mol of ethene, it being ensured—in a manner known per se—that the ethene or the oxygen only comes into contact with the catalyst before it comes into contact with the other reactants (for example, WO-A-96/26003) or the procedure is carried out otherwise, in a known manner, so that explosive gas mixtures are avoided.

The working-up of the reaction gas is also carried out in a conventional manner. In this context, reference may be made, for example, to the publications stated at the outset.

In the following example, the invention is explained in more detail with reference to the figure.

EXAMPLE 5910 m³(S.T.P)/h of hydrogen chloride at a temperature of 150° C. and 1600 m³(S.T.P)/h of oxygen, heated to 110° C., are passed together into the reactor 2 via the line 1. 3000 m³(S.T.P.)/h of ethylene are heated together with the recycled gas to 150° C. and fed to the reactor 2 via the line 3. The reactor 2 contains 40 t of fluidized-bed catalyst (alumina having a copper content of 4% by weight) with the following particle distribution:

| Particle size [μm] | Fraction (undersize) [% by weight] |
|---|---|
| <20 | 4 |
| <32 | 6 |
| <41 | 26 |
| <50 | 54 |
| <61 | 82 |
| <82 | 96 |

The heat of reaction is removed via a hot water circulation with production of steam. For separating off entrained catalyst particles in the upper part of the reactor, after leaving the fluidized bed the reaction gas flows through the superfine filter 4, in which the catalyst is virtually completely separated off. The reaction gas freed from the catalyst and having the temperature of 210° C. is passed via the line 5 into the quench column 6, where the production water is condensed and is fed via the line 7 to the wastewater treatment. The copper content of the quench water is <0.05 mg/l. The top stream, essentially comprising EDC and recycled gas, is fed via the line 8 to the EDC working-up.

The superfine filter 4 is cleaned with control by pressure difference, via the line 9 using nitrogen, which is heated to 180° C. in the preheater 10. The retention rate is >99.99%.

What is claimed is:
1. A process for the preparation of 1,2-dichloroethane by reacting ethene with hydrogen chloride and oxygen or by an oxygen-containing gas over a copper-containing fluidized-bed catalyst, wherein all the catalyst particles up to a size of 1 μm are retained inside the reactor by filtration.

2. The process according to claim 1, wherein the filtration is effected by means of a material selected from the group consisting of filter candles, bag filters or cartridge filters.

3. The process according to claim 2, wherein filter candles of sintered metal or of ceramic are used.

4. The process as claimed in claim 3, wherein filter candles of sintered metal or of ceramic are used.

* * * * *